United States Patent [19]

Curnutt

[11] Patent Number: 5,132,259
[45] Date of Patent: Jul. 21, 1992

[54] METHOD FOR REACTIVATING CATALYSTS USED IN CATALYTIC VAPOR PHASE PROCESS FOR PRODUCING DIHYDROCARBYL CARBONATES

[75] Inventor: Gerald L. Curnutt, Midland, Mich.

[73] Assignee: The Dow Chemical Company, Midland, Mich.

[21] Appl. No.: 688,464

[22] Filed: Mar. 1, 1991

Related U.S. Application Data

[60] Division of Ser. No. 97,882, Sep. 17, 1987, Pat. No. 5,004,827, which is a continuation-in-part of Ser. No. 871,725, Jun. 6, 1986, abandoned.

[51] Int. Cl.$^5$ .................. B01J 23/94; B01J 27/32; B01J 38/44; B01J 38/42
[52] U.S. Cl. .................................. 502/37; 502/35; 502/181; 502/225
[58] Field of Search .................. 502/35-37, 502/181, 225

[56] References Cited

U.S. PATENT DOCUMENTS

| | | | |
|---|---|---|---|
| 1,848,723 | 3/1932 | Jaeger | 558/277 |
| 2,113,028 | 4/1938 | Kuentzel | 558/277 |
| 3,232,889 | 2/1966 | Bellis | 502/225 |
| 3,479,392 | 11/1969 | Stern et al. | 558/277 |
| 3,501,539 | 3/1970 | Olson et al. | 570/235 |
| 3,624,170 | 11/1971 | Wakiyama et al. | 502/225 |
| 3,642,858 | 2/1972 | Freuel et al. | 558/277 |
| 3,846,468 | 11/1974 | Perrotti et al. | 558/277 |
| 3,952,045 | 4/1976 | Gaemzler et al. | 558/277 |
| 3,980,690 | 9/1976 | Cipriani et al. | 558/277 |
| 3,980,690 | 9/1976 | Cipriani et al. | 558/277 |
| 4,069,268 | 1/1978 | Siskin et al. | 558/277 |
| 4,361,519 | 11/1982 | Halgren | 558/277 |
| 4,378,275 | 5/1983 | Adamson | 204/119 |
| 4,410,464 | 10/1983 | Halgren | 558/277 |
| 4,625,044 | 11/1986 | Curnutt | 558/277 |

FOREIGN PATENT DOCUMENTS 615379  2/1961  Canada .

OTHER PUBLICATIONS

Romano et al., *Ind. Eng. Chem. Prod. Res. Dev.*, 19, 396 (1980).

Saegusa et al., *J. Org. Chem.*, 35 (9), 2976-2978 (1970).

*Primary Examiner*—Paul E. Konopka

[57] ABSTRACT

A process for the preparation of dihydrocarbyl carbonates comprising contacting an alkanol such as methanol, carbon monoxide and oxygen with a heterogeneous catalyst which comprises a metal halide such as cupric chloride or a mixed metal halide such as cupric chloride/potassium chloride impregnated on an appropriate support such as activated carbon; and a process for reactivating metal halide catalysts supported on porous carrier materials comprising drying and then contacting the supported catalysts with a gaseous stream of hydrogen halide for a period of time which is sufficient to convert all of the metal present in whatever form to the corresponding metal halide.

12 Claims, No Drawings

METHOD FOR REACTIVATING CATALYSTS USED IN CATALYTIC VAPOR PHASE PROCESS FOR PRODUCING DIHYDROCARBYL CARBONATES

CROSS REFERENCE TO RELATED APPLICATION

This is a divisional of application Ser. No. 097,882, filed Sep. 17, 1987 now issued as U.S. Pat. No. 5,004,827 which is a continuation in part of Applicant's co-pending application Ser. No. 871,725, filed Jun. 6, 1986 now abandoned.

BACKGROUND OF THE INVENTION

This invention relates to the carbonylation of alkanols. More specifically, it pertains to a process for carbonylating alkanols in the vapor phase in the presence of a heterogeneous catalyst to produce dihydrocarbyl carbonates.

This invention also relates to a method for reactivating the heterogeneous catalyst used in the above process for carbonylating alkanols in the vapor phase to produce dihydrocarbyl carbonates.

The carbonates produced by this invention are well-known and are useful as synthetic lubricants, solvents and chemical intermediates in the preparation of polymeric derivatives such as clear plastics.

The traditional method for producing carbonates involves contacting phosgene with an appropriate alcohol. See Drake et al., *J. Am. Chem. Soc.*, 52, 3720 (1960) and U.S. Pat. No. 2,379,250. This method results in the production of hydrogen chloride and thereby leads to the undesirable production of chlorine-containing by-products. In particular, the use of secondary alcohols leads to a significant formation of alkyl chlorides. Attempts to neutralize the hydrogen chloride have led to processing difficulties.

Other methods of producing carbonates generally involve the homogeneous liquid phase reaction of an alkanol, carbon monoxide and oxygen in the presence of a catalyst. For example, U.S. Pat. No. 4,360,477 describes a method for carbonylating alkanols with carbon monoxide and oxygen at elevated temperatures in the presence of copper salts. U.S. Pat. No. 4,370,275 discloses a process for preparing carbonates by reacting an alcohol, carbon monoxide and oxygen in the presence of a catalyst system containing copper, chemically bonded oxygen, chemically bonded halogen and at least one nitrogen base. The oxidative carbonylation process claimed in U.S. Pat. No. 4,426,331 involves the reaction of carbon monoxide, oxygen and an alcohol in the presence of a copper compound and a sulfone. U.S. Pat. No. 4,218,391 indicates that high acidity in carbonylation reactions involving metal salts leads to significant formation of by-products.

The above processes utilizing a homogeneous process require elaborate separation techniques to separate the organic base promoter in the azeotropic mixtures which can form between the dialkyl carbonate and the by-product water or unreacted alkanol. In addition, complex distillation steps are necessary to recover the catalysts for recycle to the processes. Due to the highly corrosive nature of most solutions containing copper halides and alkanols, expensive materials of construction are required for the reaction vessels and pipelines.

The above processes also do not provide for an efficient method of regenerating the catalysts used therein.

Most catalysts can be regenerated by being subjected to acidic conditions. However, highly acidic conditions in the actual reaction mixture can lead to significant by-product formation. Therefore, over-acidification of the catalyst can lead to lower selectivities.

A process for the catalytic production of dihydrocarbyl carbonates is needed that would eliminate the above problems regarding separation and distillation and that would facilitate the regeneration of the catalyst utilized. An efficient method for regenerating the catalyst is also needed that would not interfere with the selectivity of the catalyst.

SUMMARY OF THE INVENTION

The present invention is such a process for the production of dihydrocarbyl carbonates and avoids many of the problems heretofore encountered. The process of the present invention comprises contacting, in the vapor phase, an alkanol, carbon monoxide and oxygen with a heterogeneous catalyst containing a metal halide or mixed metal halide impregnated on an appropriate support under reaction conditions sufficient to form a dihydrocarbyl carbonate. This heterogeneous process effectively eliminates the need for elaborate separation techniques and complex distillation steps which were heretofore necessary in order to separate the catalyst from the reaction product. The supported catalyst is easily regenerated and the process can be carried out under relatively mild conditions while minimizing the production of unwanted by-products. Furthermore, no organic base promoter, such as pyridine, is needed since the support serves this function.

Another aspect of the present invention involves a method for reactivating the supported heterogeneous catalyst used in the aforementioned carbonylation reaction. The regeneration method comprises drying and contacting the catalyst with a gaseous stream of hydrogen halide for a period of time which is sufficient to convert all of the metal present in whatever form to the corresponding metal halide. This regeneration process unexpectedly allows the carbonylation catalyst to be treated under strongly acidic conditions without adversely affecting the performance and selectivity of the catalyst.

DETAILED DESCRIPTION OF THE INVENTION

The metal halide useful in the practice of the present invention can be any metal halide that will effectively catalyze the carbonylation reaction contemplated herein. The metal is preferably selected from the metals in Groups VIIIA or IB. Preferred metals include copper, nickel, iron and cobalt. The metal is most preferably copper. The halide can be chloride, bromide, iodide or fluoride and is most preferably chloride. Preferred metal halides include cupric chloride, nickel chloride and iron chloride with cupric chloride being most preferred.

Mixed metal halide herein refers to a combination of the metal halide described above with a second metal halide. The metal of the second metal halide is selected from Groups IA or IIA. Typical metals that can be used in the second metal halide of the present invention include potassium, sodium, lithium, magnesium, cesium and calcium. The metal is preferably selected from Group IA with potassium being the most preferred metal. The halide can be chloride, bromide, iodide or fluoride and is most preferably chloride. Preferred mixed metal halides include cupric chloride/potassium chloride and cupric chloride/magnesium chloride with cupric chloride/potassium chloride being most preferred.

Any support which will withstand the carbonylation conditions described herein can be used in the process of the present invention. However, activated carbon is superior to other supports that may be used. The use of activated carbon as a support results in a significantly higher rate of reaction than the use of other commonly known supports. Furthermore, the selectivity of the reaction toward the dihydrocarbonyl carbonate based on the amount of carbon monoxide fed to the reaction is higher when activated carbon is used as the support in comparison to other commonly used supports. It is preferred to use an acid-washed lignite activated carbon having a particle size in the range from 0.85 to 1.70 mm in the process of the present invention.

The metal halide may be supported on the carrier material by any standard impregnation technique such as that disclosed in Experimental Methods in Catalytic Research, Vol. II, edited by R. B. Anderson and P. T. Dawson, Academic Press, New York, 1978. In the case of a mixed metal halide, the two metal halides may be mixed together and impregnated onto the support simultaneously or the metal halides may be impregnated separately.

Alcohols useful in this invention include any alcohol which is vaporizable under the reaction conditions. Preferred alcohols correspond to the formula $R^1OH$ wherein $R^1$ is $C_{1-6}$ alkyl, $C_{3-6}$ cycloalkyl, or benzyl. $R^1$ is preferably $C_{1-6}$ alkyl, more preferably methyl, ethyl or propyl, and most preferably methyl.

Preferred alcohols include methanol, ethanol, propanol, butanol, pentanol, hexanol, cyclopropanol, cyclobutanol, cyclopentanol, cyclohexanol and benzyl alcohol. More preferred alcohols are methanol, ethanol, propanol, butanol, pentanol and hexanol. Even more preferred alcohols are methanol, ethanol or propanol, with methanol being most preferred.

This process prepares dihydrocarbonyl carbonates, wherein the hydrocarbyl moiety corresponds to the hydrocarbon portion of the alcohol used in the preparation. Preferred carbonates correspond to the formula

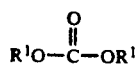

wherein $R^1$ is $C_{1-6}$ alkyl, $C_{3-6}$ cycloalkyl, or benzyl. $R^1$ is preferably $C_{1-6}$ alkyl, more preferably methyl, ethyl or propyl, and most preferably methyl.

Examples of carbonates prepared by this invention include dimethyl carbonate, diethyl carbonate, dipropyl carbonate, dibutyl carbonate, dipentyl carbonate, dihexyl carbonate, dicyclopropyl carbonate, dicyclobutyl carbonate, dicyclopentyl carbonate, dicyclohexyl carbonate, dibenzyl carbonate, methylethyl carbonate, ethylpropyl carbonate, methylpropyl carbonate and the like. Preferred carbonates prepared by this process include dimethyl carbonate, diethyl carbonate, dipropyl carbonate, dibutyl carbonate, dipentyl carbonate and dihexyl carbonate. Even more preferred carbonates are dimethyl carbonate, diethyl carbonate and dipropyl carbonate. The most preferred carbonate prepared by this invention is dimethyl carbonate.

In general, the alcohol or mixture of alcohols is contacted with oxygen and carbon monoxide under carbonylation conditions so as to prepare a carbonate. In the embodiment wherein a mixture of alcohols is used, the carbonates prepared are a mixture of symmetrical and unsymmetrical carbonates. When a single alcohol is used, the product is a symmetrical carbonate. The symmetrical dihydrocarbyl carbonates are the preferred carbonates.

The process of this invention involves contacting carbon monoxide, oxygen and an alcohol in the vapor phase and passing them over the supported metal halide described hereinbefore. The process of this invention can be illustrated by the equation

wherein $R^1$ is as defined hereinbefore. The ratio of carbon monoxide to the alcohol can be any mole ratio which results in the preparation of the dihydrocarbyl carbonates. Preferably, the ratio of carbon monoxide to the alcohol is between about 1:1 and about 1000:1 moles. More preferably, the ratio of carbon monoxide to alcohol is between about 1:1 and about 100:1 moles, and most preferably, the ratio of carbon monoxide to alcohol is between about 1:1 and about 10:1 moles. The ratio of oxygen to alcohols is any ratio which results in the preparation of the dihydrocarbyl carbonates. Preferably, the ratio of oxygen to alcohol is between about 1:1 and about 1:1000 moles. More preferably, the ratio of oxygen to alcohol is between about 1:1 and about 1:100 moles. Most preferably, the ratio of oxygen to alcohol is between about 1:1 and about 1:10 moles. The ratio of oxygen to carbon monoxide is any ratio which results in the preparation of the dihydrocarbyl carbonates. Preferably, the ratio of oxygen to carbon monoxide is between about 1:1 and about 1:1000 moles. More preferably, the ratio of oxygen to carbon monoxide is between about 1:1 and about 1:100 moles, and most preferably, the ratio of oxygen to carbon monoxide is between about 1:1 and about 1:10 moles.

The oxygen can be added to the reaction mixture as pure molecular oxygen or diluted with an inert gas such as nitrogen or argon. It is preferred to keep the oxygen concentration at no more than 10 mole percent of the entire reaction feed so as to avoid the formation of explosive mixtures.

This process can be performed at any temperature and pressure at which the reaction proceeds. Preferred temperatures are between about 20° C. and about 150° C., with between about 90° C. and about 125° C. being more preferred. The most preferred temperatures are between about 115° C. and about 125° C. The pressure can be atmospheric or superatmospheric pressure. Preferred pressures are between about 1 and about 100 atmospheres, with between about 15 and about 25 atmospheres being most preferred.

The reaction mixture feed gas flow rate, expressed as gas hourly space velocity, can be between about 100 and about 50,000 ($Hr^{-1}$), and most preferably, between about 1,000 and about 2,000 ($Hr^{-1}$). The dihydrocarbyl carbonate can be recovered from the reaction mixture by methods well-known in the art. One particularly desirable method is the use of extractive distillation of the condensed reaction product.

The process of this invention can be performed in either a fixed or fluid bed reactor using either continuous or batch processing methods. It is preferred to use a fixed bed reactor and a continuous mode of operation.

One way of expressing the reaction rate at which product is produced is by the use of a turnover number. A turnover number is defined as the number of moles of product produced per gram atom of metal in the catalyst per second. It is preferred that at least about $5.0 \times 10^{-5}$ moles of product are produced per gram atom of metal in the catalyst per second. It is more preferred that at least about $2.3 \times 10^{-4}$ moles of product are produced per gram atom of metal in the catalyst per second. It is even more preferred that at least about $4.5 \times 10^{-4}$ moles of product are produced per gram atom of metal in the catalyst per second. In the most preferred embodiment, at least about $5.0 \times 10^{-4}$ moles of product are produced per gram atom of metal in the catalyst per second. In the case of a mixed metal halide, the metal of the second metal halide is not considered in determining the turnover number or reaction rate. As discussed above, the second metal halide is the metal halide wherein the metal is selected from Groups IA or IIA. Selectivities to the dihydrocarbyl carbonate based on the alcohol preferably range from at least about 75 to 85 percent.

The other aspect of the present invention involves regeneration of the catalyst hereinbefore described. After many hours of use, the activity of the catalyst as measured by the turnover number, i.e. the number of moles of carbonate produced per gram atom of copper in the catalyst per second, decreases. The regeneration method provides a sequence of catalyst treatment steps comprising drying the catalyst and contacting the catalyst with a gaseous stream of hydrogen halide, preferably diluted with an inert gas, at a sufficient temperature and for a sufficient period of time to convert essentially all of the metal present in whatever form in whatever form to the metal halide. This regeneration process results in the regenerated catalyst showing activity comparable to fresh catalyst.

Without wishing to be bound by any theory, it is believed that the metal halide catalysts of this invention are deactivated due to loss of the halide ligand which is replaced by hydroxide. The hydroxide is in turn replaced by the halide by the regeneration process of this invention.

The regeneration process basically comprises two major steps. The first step comprises heating the catalyst in the presence of an inert gas at a sufficient temperature and for a sufficient amount of time so as to remove moisture. The second step involves subjecting the dried catalyst to gaseous hydrogen halide which has preferably been diluted with an inert gas or air for a sufficient amount of time and at an appropriate temperature to effectively reactivate the catalyst. If desired, the regenerated catalyst may be freed of adsorbed HCl by purging with an inert gas.

Typical inert gases useful in the present invention include nitrogen, helium and argon, with nitrogen and helium being preferred. The most preferred inert gas for the first step is nitrogen. Air is most preferred for the second step for reasons of convenience and economy.

The first or drying step can be carried out at any temperature sufficient to effectively remove a substantial amount of moisture from the catalyst. The precise amount of moisture removed from the catalyst is not critical but should be an amount sufficient to prevent substantial interference with catalytic activity. Drying temperatures useful in the practice of this invention range from about 90° C. to about 300° C., with about 115° C. to about 140° C. being preferred. Typical first step drying times range from about 0.1 to about 24 hours, with 2 to 4 hours being preferred. The first step can be carried out at any pressure sufficient for elimination of moisture. Typical pressures range from about 0.1 to about 500 psi with atmospheric pressure being preferred for convenience. The inert gas flow rate can range from between about 0.025 to about 250 cc (STP) per cc of catalyst per hour. Preferably, the inert gas flow rate ranges between 10 and 50 cc (STP) per cc of catalyst per hour, with about 30 cc (STP) per cc of catalyst per hour being most preferred.

The hydrohalogenation step can be carried out at any temperature sufficient to reactivate the catalyst. Typical temperatures range from about ambient temperature to about 300° C. and preferably range from about 110° C. to about 150° C. The catalyst is subjected to hydrohalogenation from between about 0.1 to about 24 hours with between about 0.5 and 2 hours being preferred. Typical pressures involved in the hydrohalogenation step range between about 0.1 to about 500 psi with atmospheric again being preferred for convenience. The typical gas flow rates in the hydrohalogenation step range from between about 0.025 to about 250 cc (STP) per cc of catalyst per hour with between about 20 and about 60 cc (STP) per cc of catalyst per hour being preferred. When an inert gas or air is used to dilute the hydrogen halide, the hydrogen halide is present in the inert gas or air in concentrations ranging from about 0.1 to about 99 mole percent based on the inert gas or air, with between about 5 and about 20 mole percent of hydrogen halide being preferred.

SPECIFIC EMBODIMENTS

The following examples are included for the purposes of illustration only and are not to be construed to limit the scope of the invention or claims. Unless otherwise indicated, all parts and percentages are by weight.

EXAMPLE 1

On a commercial activated carbon (DARCO*, 20 g, 0.85-1.70 mm) is supported 2.5 g of $CuCl_2$ from an ethanol solution by standard impregnation techniques. The dried catalyst is analyzed as 4.37 weight percent copper. Into a ½-inch outside diameter flow reactor operated at 115° C. and at 20 atm pressure is loaded 1.6 g of catalyst. A flow consisting of 80 cc (STP) per minute of CO and 13 cc (STP) per minute of oxygen is passed through the reactor. Liquid methanol is fed to a vaporizer operated at 185° C. with an LC pump which allows small amounts of $CH_3OH$ to be added to the system under pressure. A flow of $CH_3OH$ vapor of 30 cc (STP) per minute is introduced into the $CO/O_2$ feed stream prior to flowing through the reactor. The reaction products are continuously monitored on-line by standard gas chromatography techniques. Dimethyl carbonate is produced at a rate of 5.3 to $5.5 \times 10^{-4}$ moles per gram atom of copper per second with 80 percent selectivity based on methanol.

EXAMPLE 2

A $CuCl_2 \cdot KCl$ catalyst (20 weight percent $CuCl_2$ and 5 weight percent KCl) is supported on lignite activated carbon by standard impregnation techniques. A feed composed of 60 mole percent CO, 25 mole percent $CH_3OH$ and 15 mole percent $O_2$ at a gas hourly space velocity of 1800 $hr^{-1}$ is fed to a ½ inch outside diameter flow reactor operated at 110° C. and 20 atmospheres pressure. The reaction products are continuously monitored on-line by standard gas chromatography techniques. Dimethyl carbonate is produced at a rate of $6.0 \times 10^{-4}$ moles of dimethyl carbonate per gram atom of copper per second.

COMPARATIVE EXAMPLE 1

Not an embodiment of this invention

Example 2 is repeated with the only difference being that a different catalyst is used in place of the $CuCl_2.KCl$ on activated carbon. The catalyst is prepared by dissolving poly-4-vinylpyridine in methanol and adding this solution to CuCl in $CH_3CN$ according to the process described in U.S. Pat. No. 3,980,690. Dimethyl carbonate is produced at a rate of $0.6 \times 10^{-4}$ moles of dimethyl carbonate per gram atom of copper per second. This comparative example demonstrates the superiority of $CuCl_2.KCl$ supported on activated carbon as a catalyst in the production of dimethyl carbonate.

EXAMPLE 3

The procedure used in Example 1 is repeated with the only differences being that mixed metal halide catalysts are used in place of the $CuCl_2$ catalyst in successive runs and that the activity of the different catalyst systems is measured as a function of time. These results are shown in Table I below.

TABLE I

| Catalyst* | Turnover Number $\times 10^4$ (moles of DMC per g atom of Cu per sec) Time (hours) | | | | | |
|---|---|---|---|---|---|---|
| | 20 | 30 | 40 | 50 | 60 | 90 |
| $CuCl_2$ | 5.3 | 4.7 | 4.4 | 3.8 | 3.6 | — |
| $CuCl_2/KCl$ | 5.2 | 5.3 | 5.3 | 5.2 | 5.1 | 3.8 |
| $CuCl_2/MgCl_2$ | 4.5 | 4.4 | 4.5 | 4.6 | 4.4 | 3.6 |

*20 Weight percent $CuCl_2$ based on the total weight of catalyst
5 Weight percent additive (KCl or $MgCl_2$) based on total weight of catalyst The data shown above demonstrate that while $CuCl_2$ used alone has an initially slightly higher activity, the addition of 5 weight percent of KCl or $MgCl_2$ as an additive retards the rate of the deactivation of the catalyst system.

EXAMPLE 4

The reactor in Example 1 is purged with nitrogen and cooled to room temperature. The catalyst of Example 1 is heated to 125° C. in nitrogen (125 cc STP per minute) and held at that temperature for 2 hours to remove moisture. The catalyst is chlorinated by passing a mixture of 10 percent HCl/90 percent $N_2$ (175 cc STP per minute) through the reactor for 3 hours and then cooling the catalyst to room temperature while maintaining the HCl/$N_2$ flow. The reactivated catalyst exhibits an activity of $5.1 \times 10^{-4}$ moles of dimethyl carbonate per gram atom of copper per second, indicating that the activity of the aged catalyst is almost completely returned to that of the fresh catalyst.

EXAMPLE 5

A $CuCl_2$ catalyst is subjected to neutron activation and x-ray diffraction measurements when it is fresh, when it has been used about 90 hours in a procedure as given in Example 1, and when it has been treated in a regeneration process where the catalyst is treated for one hour in flowing 10% HCl/90% $N_2$ followed by a three hour $N_2$ purge. These results are given in Table II below.

TABLE II

Chemical Analysis by Neutron Activation and X-ray Diffraction Measurements on Selected Darco-Supported $CuCl_2$ Catalysts

| Catalyst Sample | Copper Crystalline Phases | Copper Loading (wt %) | Ratio Chloride/Copper (wt %) |
|---|---|---|---|
| Fresh (10.3 wt % $CuCl_2$ | — | 5.1 ± 0.2 | 1.10 (1.12)① |
| Used (90 hours) | Cu(OH)Cl $Cu_2(OH)_3Cl$ | 5.1 ± 0.2 | 0.24 |
| HCl Treated② | $Cu_2(OH)_3Cl$ | 5.2 ± 0.3 | 1.12 |

①Theory
②Treatment: One hour in flowing 10% Hcl/$N_2$ at 125° C. followed by three-hour $N_2$ purge The information in Table II shows that the regeneration process results in a regenerated catalyst not significantly different in copper crystalline phases, weight ratio of chloride to copper or in copper loading from a fresh catalyst.

EXAMPLE 6

The procedure followed in Example 1 is repeated using a $CuCl_2$ catalyst supported on activated carbon which undergoes a regeneration process as described in Example 4. The activity of the catalyst as indicated by the turnover number is shown in Table III. The data is collected over a 400-hour period.

TABLE III

| Catalyst | Starting T.N.* $\times 10^4$ | Ending T.N.* $\times 10^4$ | Elapsed time (hr) | % decrease |
|---|---|---|---|---|
| fresh | 4.9 | 3.1 | 40 | 40 |
| regenerated one time | 4.6 | 3.2 | 40 | 30 |
| regenerated two times | 4.5 | 3.2 | 50 | 27 |
| regenerated three times | 4.8 | 3.2 | 90 | 32 |
| regenerated four times | 4.3 | 2.6 | 100 | 39 |

*T.N. = turnover number (moles of DMC per g atom of Cu per sec

The data in the above table shows that the regenerated catalyst shows comparable activity with a fresh catalyst and further suggests that the regenerated catalyst is actually more stable than a fresh catalyst as it takes longer for the catalyst activity to decrease.

The above examples show that a catalyst comprising a metal halide or a mixed metal halide supported on activated carbon is effective in catalyzing the formation of dihydrocarbyl carbonate. Further, the examples demonstrate that it is possible to simply and effectively regenerate such a catalyst.

What is claimed is:

1. A process for reactivating supported heterogeneous metal halide or mixed metal halide catalysts, which have been deactivated in a vapor phase process for carbonylating alkanols to produce dihydrocarbyl carbonates comprising contacting oxygen, carbon monoxide and an alkanol in the presence of the catalyst, comprising drying, and then contacting the supported catalyst with a gaseous stream of hydrogen halide diluted with inert gas or air or mixtures thereof for a period of time which is sufficient to convert essentially all of the metal present in whatever form to the corresponding metal halide.

2. The process of claim 1 wherein the metal halide or mixed metal halide is supported on activated carbon.

3. The process of claim 2 wherein the activated carbon is acid-washed lignite carbon.

4. The process of claim 3 wherein the metal halide is cupric halide.

5. The process of claim 4 wherein the cupric halide is cupric chloride.

6. The process of claim 3 wherein the mixed metal halide consists of cupric chloride and potassium chloride.

7. The process of claim 5 wherein the hydrogen halide is hydrogen chloride.

8. The process of claim 7 wherein in the hydrogen chloride is diluted with an inert gas.

9. The process of claim 8 wherein the hydrogen chloride is diluted with air.

10. The process of claim 1 wherein the drying step is conducted at a temperature of from about 115° C. to about 140° C. and the contact with hydrogen halide is conducted at a temperature of from about 110° C. to about 150° C.

11. A process for reactivating an activated carbon-supported cupric chloride catalyst which has been deactivated in a vapor phase process for carbonylating alkanols to produce dihydrocarbyl carbonates comprising contacting oxygen, carbon monoxide and an alkanol in the presence of the catalyst, comprising
    (1) heating the supported catalyst to 125° C. in the presence of a 125 cc (STP) per minute flow of nitrogen,
    (2) holding the catalyst at 125° C. in the presence of the nitrogen for about 2 hours,
    (3) passing a mixture of 10 percent hydrogen chloride/90 percent air at a flow rate of 175 cc (STP) per minute over the catalyst for about 3 hours, and
    (4) cooling the catalyst to room temperature while maintaining the hydrogen chloride/air flow.

12. A process for reactivating an activated carbon-supported cupric chloride/potassium chloride catalyst, which has been deactivated in a vapor phase process for carbonylating alkanols to produce dihydrocarbyl carbonates comprising contacting oxygen, carbon monoxide and an alkanol in the presence of the catalysts, comprising
    (1) heating the supported catalyst to 125° C. in the presence of a 125 cc (STP) per minute flow of nitrogen,
    (2) holding the catalyst at 125° C. in the presence of the nitrogen for about 2 hours,
    (3) passing a mixture of 10 percent hydrogen chloride/90 percent air at a flow rate of 175 cc (STP) per minute over the catalyst for about 3 hours, and
    (4) cooling the catalyst to room temperature while maintaining the hydrogen chloride/air flow.

* * * * *